United States Patent [19]

Mettler et al.

[11] Patent Number: 5,003,099

[45] Date of Patent: Mar. 26, 1991

[54] METHOD FOR THE PRODUCTION OF AMINOCYANOACETAMIDE

[75] Inventors: Hans P. Mettler, Brig-Glis; Felix Previdoli, Brig, both of Switzerland

[73] Assignee: Lonza Ltd., Gampel/Valais, Switzerland

[21] Appl. No.: 348,054

[22] Filed: May 5, 1989

[30] Foreign Application Priority Data

May 17, 1988 [CH] Switzerland .................. 01861/88

[51] Int. Cl.$^5$ .......................................... C07C 255/28
[52] U.S. Cl. .................................................. 558/445
[58] Field of Search ......................................... 558/445

[56] References Cited

U.S. PATENT DOCUMENTS 2,367,455 1/1945 Bock et al. ..................... 558/445

FOREIGN PATENT DOCUMENTS 0029567 6/1981 European Pat. Off. .
52-21326 2/1977 Japan .

OTHER PUBLICATIONS

Chem. Abstracts vol. 93, abst. no. 204030q (1980).
P. A. S. Smith, The Chemistry of Open-Chain Organic Nitrogen Compounds vol. 2 (W. A. Benjamin, Inc., 1966), p. 380.
Hackh's Chemical Dictionary, McGraw-Hill Book Co., 1983, pp. 26, 457.
Streitwieser, Jr. et al., Introduction to Organic Chemistry, Third Ed (1984), Macmillan Publ. pp. 253, 702.

*Primary Examiner*—Joseph Paul Brust
*Assistant Examiner*—Jacqueline Haley
*Attorney, Agent, or Firm*—Horst M. Kasper

[57] ABSTRACT

A large-scale industrial process for the production of aminocyanoacetamide is disclosed. A starting material is cyanoacetic acid ester, which is treated with a nitrous acid in a first step to a corresponding hydroxyiminocyanoacetic acid ester. The hydroxyiminocyanoacetic acid ester is then hydrogenated and, in a following step, treated with ammonia for obtaining the final product aminocyanoacetamide.

18 Claims, No Drawings

METHOD FOR THE PRODUCTION OF AMINOCYANOACETAMIDE

BACKGROUND OF THE INVENTION

1. Field of the Invention

The invention relates to a new, large-scale industrially employable method for the production of aminocyanoacetamide. Aminocyanoacetamide is an interesting intermediate product for the production of, for example, imidazoles, pyridazines, purines, and pteridines.

2. Brief Description of the Background of the Invention Including Prior Art

Several methods are known for the production of aminocyanoacetamide or, respectively, for the production of aminocyanoacetic esters.

A method for the production of aminocyanoacetic acid ethyl ester from hydroxy-iminocyanoacetic acid ethyl ester is known from the German Patent Application Laid Open DE-OS No. 2,700,733 by way of hydrogenation with Raney nickel. The yields achievable according to the reference amount to about 65%. In addition to the unsatisfactory yield and the low quality of the isolated product, it is a big disadvantage that the catalyst can only be regenerated and recirculated with a relatively large expenditure. Such an expenditure is not justifiable for a large-scale industrial production.

It is known from the publication Logeman et al., Chemistry and Industry (1980), p. 541, that hydroxy-iminocyanoacetic acid ethyl ester can be reacted, with sodium dithionite and in the presence of ethanol as a solvent with a yield of 81% for the raw product, into the aminocyanoacetic acid ethyl ester. The generated sulfate waste as well as the application of fire-hazardous ether is a disadvantage of this method. Such methods and processes are avoided wherever possible in view of the environmental problems associated with the disposal of salt wastes.

Finally, it is known from the publication Taylor et al., Journal of the American Chemical Society, 98, 2301, (1976), that hydroxy-iminocyanoacetic acid benzyl ester can be reacted in the presence of aluminum amalgam and ester as a solvent and, in a second step, with methane sulfonic acid, with a yield of 53%, into the methane sulfonate of the aminocyanoacetic acid benzyl ester. This method can no longer be discussed for a technical application in view of the problems associated with the waste disposal of the mercury catalyst.

The method of Smith et al., Journal of the American Chemical Society 76, 6080, (1954), is associated with the same disadvantages. According to the reference, the starting material is hydroxy-iminocyanoacetamide, which is directly hydrogenated with aluminum amalgam to aminocyanoacetamide, with a yield of 59%.

SUMMARY OF THE INVENTION

1. Purposes of the Invention

It is an object of the present invention to provide a method without the recited disadvantages and which allows to produce aminocyanoacetamide, starting from a large-scale industrially available starting material, on an industrial scale, and in substantially environment-friendly manner.

Is is a further object of the present invention to avoid the use of difficultly regeneratable catalysts.

It is yet a further object of the present invention to provide a process for the production of aminocyanoacetamide with high yields.

These and other objects and advantages of the present invention will become evident from the description which follows.

2. Brief Description of the Invention

The present invention provides for a method for the production of aminocyanoacetamide. A member selected of the group consisting of cyanoacetic-acid-$(C_1-C_4)$-alkyl ester, cyanoacetic-acid-aryl-$(C_1-C_4)$-alkyl ester and mixtures thereof is treated with a nitrous acid to form a corresponding hydroxy-iminocyanoacetic acid ester. The hydroxy-iminocyanoacetic acid ester is hydrogenated with hydrogen to aminocyanoacetic acid ester in the presence of a platinum hydrogenation catalyst. The aminocyanoacetic acid ester is reacted with aqueous ammonia to the final product.

The member selected of the group consisting of cyanoacetic-acid-$(C_1-C_4)$-alkyl ester, cyanoacetic-acid-aryl-$(C_1-C_4)$-alkyl ester and mixtures thereof can be treated with an alkali nitrite to form a corresponding hydroxy-iminocyanoacetic acid ester in the presence of acid.

The hydroxy-iminocyanoacetic acid ester, prior to its reaction with hydrogen to aminocyanoacetic acid ester, can be isolated.

The hydroxy-iminocyanoacetic acid ester can be hydrogenated without isolation with hydrogen to aminocyanoacetic acid ester in the presence of a platinum hydrogenation catalyst.

The aminocyanoacetic acid ester can be isolated prior to reacting with aqueous ammonia to the final product. The aminocyanoacetic acid ester can be reacted without isolation directly with aqueous ammonia to the final product.

A member, selected of the group consisting of platinum oxide, platinum, platinum placed in amounts of from 1 to 20 weight-percent onto a carrier material, platinum placed in amounts of from 1 to 20 weight-percent onto aluminum oxide, platinum placed in amounts of from 1 to 20 weight-percent onto silicon dioxide, platinum placed in amounts of from 1 to 20 weight-percent onto barium sulfate, platinum placed in amounts of from 1 to 20 weight-percent onto calcium carbonate, platinum placed in amounts of from 1 to 20 weight-percent onto carbon, and mixtures thereof, can be employed as a platinum hydrogenation catalyst.

The hydroxy-iminocyanoacetic acid ester can be hydrogenated with hydrogen to aminocyanoacetic acid ester under a pressure of from 1 to 100 bar and at temperatures from between about 0° to 40°.

The hydroxy-iminocyanoacetic acid ester can be hydrogenated with hydrogen to aminocyanoacetic acid ester in the presence of lower aliphatic alcohols, lower aliphatic carbonic acid esters, or lower aliphatic carbonic acids serving as a solvent.

The number of carbon atoms in the molecules of the solvent can on average be less than 10. The conversion of the ester to the amide can be performed with aqueous ammonia at temperatures from between −20° to 30° C.

Preferably, 1 to 30-mol equivalents ammonia relative to 1 mol-equivalent of aminocyanoacetic acid ester is employed for reacting the aminocyanoacetic acid ester with aqueous ammonium to the final product.

Hydroxy-iminocyanoacetic acid ester can be extracted with an organic solvent from the reaction mixture. The organic phase can be washed to a neutral state. The organic phase can be dried over a drying agent. The organic phase is concentrated by evaporation. Preferably, the concentrated phase is allowed to precipitate the hydroxy-iminocyanoacetic acid ester.

The novel features, which are considered as characteristic for the invention, are set forth in the appended claims. The invention itself, however, both as to its method of operation, its products and physical requirements, together with additional objects and advantages thereof, will be best understood from the following description of specific embodiments and examples.

DESCRIPTION OF INVENTION AND PREFERRED EMBODIMENT

In accordance with the present invention, there is provided a method for the production of aminocyanoacetamide. A cyanoacetic-acid-($C_1$-$C_4$)-alkyl ester or an aryl alkyl ester in the presence of an alkali nitrite is treated with a nitrous acid to form a corresponding hydroxy-iminocyanoacetic acid ester. The alkali nitrites include sodium nitrite. This hydroxy-iminocyanoacetic acid ester is, possibly first isolated or without isolation directly, hydrogenated with hydrogen to aminocyanoacetic acid ester in the presence of a platinum hydrogenation catalyst. The aminocyanoacetic acid ester is, possibly isolated or without isolation directly, finally reacted with aqueous ammonia to the final product.

Preferably, platinum oxide or platinum is employed as a platinum catalyst, and placed in amounts of from 1 to 20 weight-percent onto a carrier material such as aluminum oxide, silicon dioxide, barium sulfate, calcium carbonate, or carbon.

The hydrogenation can be performed under a pressure of from 1 to 100 bar and at temperatures from between about 0° to 40°. The hydrogenation can be performed in the presence of lower aliphatic alcohols, lower aliphatic carbonic acid esters, or lower aliphatic carbonic acids as solvent. The number of carbon atoms in the solvents can be less than 10. The conversion of the ester to the amide can be performed with aqueous ammonia at temperatures from between −20° to 30° C.

Preferably, 1 to 30-mol equivalents ammonia are employed relative to 1 mol-equivalent of aminocyanoacetic acid ester for the reaction with aqueous ammonia.

A starting point of the invention method are the large-scale industrially available cyanoacetic acid esters. Suitable for the reaction according to the invention are the $C_1$-$C_4$-alkyl esters, such as the methyl esters, ethyl esters, propyl esters, butyl esters or tertiary butyl esters, or the arylalkyl esters, such as the benzyl ester.

In a first step, the cyanoacetic acid esters are treated with an alkali nitrate in presence of an acid in a conventional way to form the corresponding hydroxy-iminocyanoacetic acid ester, for example, according to G. Duguay, Journal of Heterocyclic Chemistry, Issue 17, p. 767, (1980). As an agent for treatment with nitrous acid, alkali nitrites are usually employed, in particular sodium nitrite. The reaction is performed in an acid medium.

The resultant hydroxy-iminocyanoacetic acid ester is in general transferred into an organic phase, from which it can be isolated if desired or, preferably, employed directly for a consecutive stage.

The consecutive stage, the hydrogenation of the hydroxy-iminocyanoacetic acid ester to the aminocyanoacetic acid ester, is performed with hydrogen in the presence of a platinum catalyst. Suitable platinum catalysts include platinum, which can be finely dispersed in amounts of from 1 to 20 weight-percent on carbon, aluminum oxide, silicon dioxide, barium sulfate, or calcium carbonate as carrier materials, or platinum oxide. Platinum is preferred as a catalyst in an amount of from 3 to 10 weight-percent dispersed on carbon. Advantageously, the platinum catalyst is employed in amounts of from 3 to 30 weight-percent, and preferably in amounts of from 10 to 15 weight-percent, as referred to the weight of the hydroxy-iminocyanoacetic acid ester.

The hydrogenation is performed according to experience at a pressure of from 1 to 100 bar, preferably at a pressure of from 6 to 10 bar, and at temperatures from 0° to 40° C., where an ambient temperature or a temperature from about 15° to 25° C. is a preferred temperature.

It is an advantage to work in the presence of a low-boiling organic solvent, such as a low aliphatic alcohol, for example, ethanol, as well as a low carbonic acid ester, for example, ethyl acetate, or a low carbonic acid, for example, acetic acid.

The hydrogenation can take place over a time ranging from about 0.5 to 10 hours, depending in each case on pressure, temperature, and catalyst amount.

The recirculation of the platinum hydrogenation catalyst after termination of the reaction, and its use for the next following step of hydrogenation, is a further advantage of the invention method.

The resultant aminocyanoacetic acid ester can be isolated and separated from the reaction solution, however, the aminocyanoacetic acid ester is preferably directly reacted with ammonia to the final product, i.e. to aminocyanoacetamide.

The reaction to aminocyanoacetamide is performed in aqueous ammonia, advantageously having a concentration of from 10 to 40 weight-percent, at temperatures of from −20° to 30° C., and preferably at a temperature of from about 0° to 5° C.

The molar ratio of ammonia to aminocyanoacetic acid ester is advantageously selected between 30:1 and 1:1, and preferably between 10:1 and 5:1.

The solvent corresponds substantially to that of the pre-stage. However, it is also possible to work only in aqueous ammonia as a solvent, i.e. without additional solvents.

The resultant aminocyanoacetamide can be obtained after conventional reprocessing with yields higher than 70%, as referred to the cyanoacetic acid ester, with a content of more than 98 weight-percent of the product.

Since the aminocyanoacetic acid ester is already a favored intermediate product for numerous syntheses, but is not very stable in storage, there is the alternative possibility of adding an acid to the reaction solution after termination of the hydrogenation, and of transforming the aminocyanoacetic ester into a salt. Salts of the aminocyanoacetic acid ester, which are particularly suitable, include the tosylates, the oxalates, or the methane sulfonates, and particularly preferred are the tosylates. These salts are distinguished by their high storage stability, easy and simple manipulation, and the possibility of a production in a very high degree of purity.

The reaction procedure can be described by the following equation (by way of example with the cyanoacetic ethylester as starting molecule):

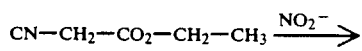

-continued

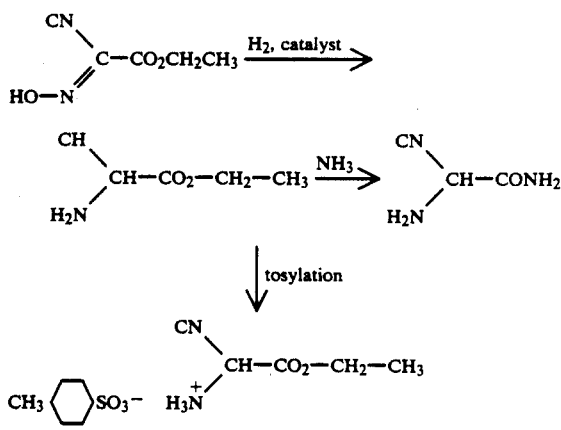

EXAMPLE 1

Production of Hydroxy-Iminocyanoacetic Acid Ethyl Ester from Cyanoacetic Acid Ethyl Ester 83.0 g of glacial acetic acid were dropped, at a temperature of 10° C. and during a time period of 30 minutes, to 113.7 g (1.0 mol) cyanoacetic acid ethyl ester and 83.2 g (1.2 mol) sodium nitrite, dissolved in 900 ml of ice water. This solution was stirred for a time period of four hours at a temperature of 20° C. 100 ml of concentrated hydrochloric acid were added to the solution, and extraction was performed with 4×150 ml of ethyl acetate. The organic phase was washed to a neutral state with 4×50 ml of ice water. The organic phase was then dried over sodium sulfate, was concentrated by evaporation to 245 g, and was left standing for 12 hours at a temperature of 4° C. The precipitated hydroxy-iminocyanoacetic acid ethyl ester was filtered off, was washed with cold ethyl acetate, and dried. 130.6 g product with a yield of 91.9% were obtained, as referred to the cyanoacetic acid ethyl ester, with a melting point of 129.5° to 131° C.

Elementary analysis for $C_5H_6N_2O_3$: found: C=41.75%, H=4.25%, N=19.11%. calculated: C=42.26%, H=4.26%, N=19.71%.

EXAMPLE 2

Production of Aminocyanoacetic Acid Methyl Ester Tosylate from Hydroxy-Iminocyanoacetic Acid Methyl Ester A solution of 18.0 g (0.14 mol) hydroxy-iminocyanoacetic acid methyl ester in 200 ml ethanol was hydrogenated, at a 10-bar hydrogen pressure and at ambient temperature, over a catalyst of 2.7 g platinum dispersed at a 5% concentration on carbon. The reaction mixture was filtered, 26.9 g (0.14 mol) toluene sulfonic acid monohydrate was added to the filtrate, 750 ml toluene were admixed, the mixture was concentrated by evaporation to 340 g and was left standing for 12 hours at 4° C. The precipitated aminocyanoacetic acid methyl ester tosylate was filtered off, was washed with toluene, and was dried. 36.9 g of product were obtained with a yield of 89.7%, as referred to the hydroxy-iminocyanoacetic acid methyl ester, with a melting point of from 162.5° to 164.5° C.

Elementary Analysis for $C_{11}H_{14}N_2O_5S$: found: C=45.80%, H=4.92%, N=9.65%. calculated: C=46.18%, H=4.93%, N=9.79%.

EXAMPLE 3

Production of Aminocyanoacetic Acid Ethyl Ester Tosylate from Hydroxy-Iminocyanoacetic Acid Ethyl Ester A solution of 20.0 g (0.14 mol) hydroxy-iminocyanoacetic acid ethyl ester in 200 ml ethanol was hydrogenated, at a 10-bar hydrogen pressure and at ambient temperature, over a catalyst of 2.6 g platinum dispersed at a 5% concentration on carbon. The reaction mixture was filtered, 26.9 g (0.14 mol) toluene sulfonic acid monohydrate were added to the filtrate, the mixture was mixed with 1200 ml of toluene, the mixture was concentrated by evaporation to 330 g, and was left standing for 12 hours at a temperature of 4° C. The precipitated aminocyanoacetic acid ethyl ester tosylate was filtered off, was washed with toluene, and was dried. 40.0 g product were obtained with a yield of 93.4%, as referred to the hydroxy-iminocyanoacetic acid ethyl ester, with a melting point of from 128° to 130° C. A product with a melting point of from 130° to 131° C. was isolated by recrystallization from ethyl acetate.

Elementary analysis for $C_{12}H_{16}N_2O_5S$: found C=47.44%, H=5.42%, N=9.21%. calculated C=48.00%, H=5.37%, N=9.33%.

EXAMPLE 4

Production of Aminocyanoacetic Acid Benzyl Ester Tosylate from Hydroxy-Iminocyanoacetic Acid Benzyl Ester A solution of 20.4 g (0.1 mol) hydroxy-iminocyanoacetic acid benzyl ester in 200 ml ethanol was hydrogenated, at a 10-bar hydrogen pressure and at ambient temperature, over a catalyst of 3.1 g platinum dispersed at a 5% concentration on carbon. The reaction mixture was filtered, 19.2 g (0.1 mol) toluene sulfonic acid monohydrate was added to the filtrate, the filtrate was then concentrated by evaporation to 150 g, was mixed with 400 ml toluene, was concentrated by evaporation to 230 g, and was left standing for 12 hours at 4° C. The precipitated aminocyanoacetic acid benzyl ester tosylate was filtered off, was washed with toluene, and was dried. 31.2 g product were obtained with a yield of 86.3%, as referred to the hydroxy-iminocyanoacetic acid benzyl ester, and had a melting point of from 171° to 172° C. A product with a melting point of from 173° to 174° C. was isolated by recrystallization from isopropanol.

Elementary analysis for $C_{17}H_{18}N_2O_5S$: found: C=55.60%, H=4.95%, N=7.82%. calculated: C=56.38%, H=5.01%, N=7.73%.

EXAMPLE 5

Production of Aminocyanoacetic Acid Tertiary Butylester Tosylate from Hydroxy-Iminocyanoacetic Acid Tertiary Butylester A solution of 21.3 g (0.1 mol) hydroxy-iminocyanoacetic acid tertiary butylester in 200 ml ethanol was hydrogenated, at a 10-bar hydrogen pressure and at ambient temperature, over a catalyst of 3.2 g platinum dispersed at a 5% concentration on carbon. The reaction mixture was filtered, 19.0 g (0.1 mol) toluene sulfonic acid monohydrate were added to the filtrate, the resulting mixture was mixed with 500 ml toluene, was concentrated by evaporation to 204 g, and was left standing for 12 hours at 4°. The precipitated aminocyanoacetic acid tertiary butylester tosylate was filtered off, was washed with toluene, and was dried. 16.2 g product with a yield of 51.1% was obtained, as referred to the hydroxy-iminocyanoacetic acid tertiary butylester, with a melting point of from 124° to 126° C. After recrystallization from a mixture of ethyl acetate/ethanol in a ratio of 3:1, a product was isolated having a melting point of from 128° to 129.5° C.

Elementary analysis for $C_{14}H_{20}N_2O_5S$: found: $C=51.15\%$, $H=6.21\%$, $N=8.65\%$. calculated: $C=51.24\%$, $H=6.14\%$, $N=8.54\%$.

EXAMPLE 6

Production of Aminocyanoacetic Acid Ethyl Ester Tosylate from Cyanoacetic Acid Ethyl Ester 12.5 g (0.21 mol) glacial acetic acid were dropped to 17.1 g (0.15 mol) cyanoacetic acid ethyl ester and 12.4 g (0.18 mol) sodium nitrite, dissolved in 135 ml ice water, at a temperature of 10° C. during a time period of 10 minutes. The solution was stirred one hour at 20° C., 15 ml of concentrated hydrochloric acid were added, and extraction was performed with 4×50 ml ethyl acetate. The organic phase was washed to neutral with 3×15 ml ice water. The organic phase was dried over sodium sulfate and concentrated by evaporation to 200 g. This solution was hydrogenated, at a 10-bar hydrogen pressure and at ambient temperature, over a catalyst of 3.2 g platinum dispersed on carbon at a concentration of 5%. The reaction mixture was filtered, a solution of 28.8 g (0.15 mol) toluene sulfonic acid monohydrate in 25 g methanol was added to the filtrate, the mixture was concentrated by evaporation to 120 g, the mixture was then admixed with 200 ml toluene, the mixture was again concentrated to 155 g, and was left standing for 12 hours at a temperature of 4° C. The precipitated aminocyanoacetic acid ethyl ester tosylate was filtered off, was washed with toluene, and was dried. After recrystallization from ethyl acetate, 33.7 g product were isolated, with a yield of 74.9%, as referred to the amount of cyanoacetic acid ethyl ester employed.

EXAMPLE 7

Production of Aminocyanoacetamide from Hydroxy-Iminocyanoacetic Acid Methyl Ester A solution of 38.6 g (0.3 mol) hydroxy-iminocyanoacetic acid methyl ester, dissolved in 200 ml methanol, were hydrogenated, at a 10-bar hydrogen pressure and at ambient temperature, over a catalyst of 3.1 g platinum, dispersed at a 5% concentration on carbon. The reaction mixture was filtered, 15 ml ice water were added to the filtrate, and the mixture was added to a solution of 9.0 g ammonia and 25 g methanol at a temperature of 0° C. The reaction mixture was stirred at 0° C. for a time period of 0.5 hour. The precipitated aminocyanoacetamide was filtered off, was washed with toluene, and was dried. A product of 18.4 g with a melting point of from 119.5° to 120.5° C. was obtained. The filtrate was concentrated to 150 ml, was mixed with 450 ml toluene, was concentrated to 300 ml, and was left standing for 12 hours at a temperature of 4° C. The precipitated aminocyanoacetamide was filtered off, was washed with toluene, and was dried. A further 6 grams of product were obtained with a melting point of from 112° to 115° C.

Total yield: 82.0%, as referred to the hydroxy-iminocyanoacetic acid methyl ester.

Elementary analysis for $C_3H_5N_3O$: found $C=36.3\%$, $H=5.1\%$, $N=40.5\%$. calculated $C=36.4\%$, $H=5.1\%$, $N=42.4\%$.

EXAMPLE 8

Production of Aminocyanoacetamide from Cyanoacetic Acid Methyl Ester (Direct Synthesis)

31.8 g (0.53 mol) glacial acetic acid were dropped to 40.0 g (0.40 mol) cyanoacetic acid methyl ester and 33.5 g (0.48 mol) sodium nitrite, dissolved in 300 ml water, at a temperature of 10° C. during a time period of 20 minutes. The solution was stirred at a temperature of 20° C. for a time period of one hour, 50.6 g (0.5 mol) concentrated hydrochloric acid were added to the solution and the solution was extracted with 6×50 ml ethyl acetate. The organic phase was washed to neutral with 2×50 ml water, was dried over sodium sulfate, and was concentrated to 150 ml and was mixed with 100 ml methanol. The solution was hydrogenated at a pressure of 6 to 10 bar hydrogen and at ambient temperature over a catalyst of 5.1 g platinum dispersed at 5% concentration on carbon. The reaction mixture was subsequently filtered, 15 ml water were added, and this mixture was added to a solution of 36.7 g (2.2 mol) ammonia in 150 ml methanol at a temperature of from 0° to 5° C. The precipitated product was filtered off after one hour, was washed with methanol, and was dried. 20.5 g aminocyanoacetamide with a melting point of from 121° to 122° C. were obtained. The filtrate was concentrated to 50 g, was placed in a cool temperature, and was filtered again, whereby an additional 8.7 g product, with a melting point of from 120° to 121° C., were isolated.

Total yield: 73.2%, as referred to the employed cyanoacetic acid methyl ester.

It will be understood that each of the steps, conditions and reagents described above, or two or more together, may also find a useful application in other types of nitrosation and hydrogenation reactions and processing procedures, differing from the types described above.

While the invention has been illustrated and described as embodied in the context of a method for production of aminocyanoacetamide, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. A method for the production of aminocyanoacetamide comprising
   nitrosating a member selected of the group consisting of cyanoacetic-acid-($C_1$–$C_4$)-alkyl ester, cyanoacetic-acid-aryl-($C_1$–$C_4$)-alkyl ester and mixtures thereof with an alkali metal nitrite to form a corresponding hydroxy-iminocyanoacetic acid ester;
   hydrogenating the hydroxy-iminocyanoacetic acid ester with hydrogen to aminocyanoacetic acid ester in the presence of a platinum hydrogenation catalyst under a pressure of from 1 to 100 bar and at temperatures from between about 0° to 40°; reacting the aminocyanoacetic acid ester with aqueous ammonia to the final product;

employing platinum placed in amounts of from 1 to 20 weight-percent onto aluminum oxide, platinum placed in amounts of from 1 to 20 weight-percent onto silicon dioxide, platinum placed in amounts of from 1 to 20 weight-percent onto barium sulfate, platinum placed in amounts of from 1 to 20 weight-percent onto calcium carbonate, platinum placed in amounts of from 1 to 20 weight-percent onto carbon, and mixtures thereof, as said platinum hydrogenation catalyst.

2. The method according to claim 1, further comprising treating the member selected of the group consisting of cyanoacetic-acid-($C_1$–$C_4$)-alkyl ester, cyanoacetic-acid-aryl-($C_1$–$C_4$)-alkyl ester and mixtures thereof with an alkali metal nitrite to form a corresponding hydroxy-iminocyanoacetic acid ester in the presence of an alkali metal nitrite.

3. The method according to claim 1, further comprising isolating the hydroxy-iminocyanoacetic acid ester, prior to its reaction with hydrogen to aminocyanoacetic acid ester.

4. The method according to claim 1, further comprising hydrogenating the hydroxy-iminocyanoacetic acid ester without isolation with hydrogen to aminocyanoacetic acid ester in the presence of a platinum hydrogenation catalyst.

5. The method according to claim 1, further comprising isolating the aminocyanoacetic acid ester prior to reacting with aqueous ammonia to the final product.

6. The method according to claim 1, further comprising reacting the aminocyanoacetic acid ester without isolation directly with aqueous ammonia to the final product.

7. The method according to claim 1, further comprising hydrogenating the hydroxy-iminocyanoacetic acid ester with hydrogen to aminocyanoacetic acid ester under a pressure of from 6 to 10 bar and at temperatures from between about 15° to 25°.

8. The method according to claim 1, further comprising hydrogenating the hydroxy-iminocyanoacetic acid ester with hydrogen to aminocyanoacetic acid ester in the presence of a lower acyclic aliphatic alcohol having up to 4 carbon atoms, a lower saturated acyclic carboxylic acid, said saturated acyclic carboxylic acid having up to 2 carbon atoms or a lower alkylester with 1 to 4 carbon atoms thereof serving as a solvent.

9. The method according to claim 8, wherein the number of carbon atoms in the molecules of the solvent is on average less than 10.

10. The method according to claim 1, wherein the conversion of the ester to the amide is performed with aqueous ammonia at temperatures from between −20° to 30° C.

11. The method according to claim 1 further comprising employing 1 to 30-mol equivalents ammonia relative to 1 mol-equivalent of aminocyanoacetic acid ester for reacting the aminocyanoacetic acid ester with aqueous ammonia to the final product.

12. The method according to claim 1 further comprising extracting hydroxy-iminocyanoacetic acid ester with an organic solvent from the reaction mixture;
washing the organic phase to a neutral state;
drying the organic phase over a drying agent;
concentrating the organic phase by evaporation; and
allowing the concentrated phase to precipitate the hydroxy-iminocyanoacetic acid ester.

13. A method for the production of aminocyanoacetamide, wherein a cyanoacetic-acid-($C_1$–$C_4$)-alkyl ester or an aryl alkyl ester in the presence of an acid is treated with an alkali metal nitrite to form a corresponding hydroxy-iminocyanoacetic acid ester, wherein this hydroxy-iminocyanoacetic acid ester is hydrogenated with hydrogen to aminocyanoacetic acid ester in the presence of a platinum hydrogenation catalyst and wherein the hydrogenation is performed under a pressure of from 1 to 100 bar and at temperatures from about 0° to 45° and wherein the aminocyanoacetic acid ester is finally reacted with aqueous ammonia to the final product;

employing platinum placed in amounts of from 1 to 20 weight-percent onto aluminum oxide, platinum placed in amounts of from 1 to 20 weight-percent onto silicon dioxide, platinum placed in amounts of from 1 to 20 weight-percent onto barium sulfate, platinum placed in amounts of from 1 to 20 weight-percent onto calcium carbonate, platinum placed in amounts of from 1 to 20 weight-percent onto carbon, and mixtures thereof, as a platinum hydrogenation catalyst.

14. The method according to claim 13, wherein the hydrogenation is performed under a pressure of from 6 to 10 bar and at temperatures from between about 15° to 25°.

15. The method according to claim 13, wherein the hydrogenation is performed in the presence of lower aliphatic alcohols, lower aliphatic carbonic acid esters, or lower aliphatic carbonic acids as solvent.

16. The method according to claim 15, wherein the number of carbon atoms in molecules of the solvents is less than 10.

17. The method according to claim 13, wherein conversion of the ester to the amide is performed with aqueous ammonia at temperatures from between −20° to 30° C.

18. The method according to claim 13, wherein 1 to 30-mol equivalents ammonia are employed relative to 1 mol-equivalent of aminocyanoacetic acid ester for the reaction with aqueous ammonia.

* * * * *